United States Patent
Dehghan Marvast (10) Patent No.: US 10,546,397 B2
(45) Date of Patent: Jan. 28, 2020

(54) RESPIRATORY MOTION COMPENSATION FOR FOUR-DIMENSIONAL COMPUTED TOMOGRAPHY IMAGING USING ULTRASOUND

(71) Applicant: KONINKLIJKE PHILIPS N.V., Eindhoven (NL)

(72) Inventor: Ehsan Dehghan Marvast, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 28 days.

(21) Appl. No.: 15/756,119

(22) PCT Filed: Sep. 5, 2016

(86) PCT No.: PCT/IB2016/055296
§ 371 (c)(1),
(2) Date: Feb. 28, 2018

(87) PCT Pub. No.: WO2017/046674
PCT Pub. Date: Mar. 23, 2017

(65) Prior Publication Data
US 2018/0247435 A1    Aug. 30, 2018

Related U.S. Application Data

(60) Provisional application No. 62/219,184, filed on Sep. 16, 2015.

(51) Int. Cl.
*G06T 11/00* (2006.01)
*A61B 6/03* (2006.01)
(Continued)

(52) U.S. Cl.
CPC .......... *G06T 11/005* (2013.01); *A61B 5/7289* (2013.01); *A61B 6/032* (2013.01);
(Continued)

(58) Field of Classification Search
CPC ............ G06T 11/005; G06T 2211/412; G06T 2207/10132; G06T 2207/10076;
(Continued)

(56) References Cited

U.S. PATENT DOCUMENTS 8,411,915 B2   4/2013   Wischmann
8,529,453 B2   9/2013   Averkiou
(Continued)

FOREIGN PATENT DOCUMENTS

DE   102012209984   12/2013
EP       2540346    1/2013
(Continued)

OTHER PUBLICATIONS

Epelman, et al., "M-mode sonography of diaphragmatic motion: description of technique and experience in 278 pediatric patients", Pediatric Radiology, Springer, vol. 35, No. 7, Jul. 1, 2005.
(Continued)

*Primary Examiner* — Jon Chang
(74) *Attorney, Agent, or Firm* — Larry Liberchuk (57) ABSTRACT

A method for determining a surrogate respiratory signal for four-dimensional computed tomography using ultrasound data includes acquiring computed tomography data with a computed tomography imaging system (402), acquiring ultrasound data with an ultrasound probe of an ultrasound imaging system (404) concurrently with acquiring the computed tomography data during one or more respiratory cycles, wherein the ultrasound probe is aligned to acquire an image of a diaphragm of a subject, synchronizing the acquired computed tomography data and the acquired ultrasound data, and determining a surrogate respiratory signal from the acquired ultrasound data.

16 Claims, 5 Drawing Sheets

(51) Int. Cl.
- *A61B 8/08* (2006.01)
- *A61B 5/00* (2006.01)
- *A61B 5/08* (2006.01)
- *A61B 6/00* (2006.01)
- *A61B 8/00* (2006.01)

(52) U.S. Cl.
CPC .......... *A61B 6/5264* (2013.01); *A61B 6/5288* (2013.01); *A61B 8/085* (2013.01); *A61B 8/4218* (2013.01); *A61B 8/4263* (2013.01); *A61B 8/486* (2013.01); *A61B 5/0803* (2013.01); *G06T 2207/10076* (2013.01); *G06T 2207/10132* (2013.01)

(58) Field of Classification Search
CPC ..... A61B 8/486; A61B 8/4218; A61B 8/4263; A61B 6/032; A61B 5/7289; A61B 8/085; A61B 6/5288; A61B 6/5264; A61B 5/0803

See application file for complete search history.

(56) References Cited

U.S. PATENT DOCUMENTS

| | | | |
|---|---|---|---|
| 8,814,793 | B2 | 8/2014 | Brabrand |
| 9,526,476 | B2 * | 12/2016 | Schwartz ............. A61B 8/4236 |
| 2004/0167389 | A1 * | 8/2004 | Brabrand ................ A61B 8/08 600/407 |
| 2006/0016006 | A1 * | 1/2006 | Whitmore, III ..... A61B 6/0442 5/601 |
| 2007/0016005 | A1 | 1/2007 | Timinger |
| 2012/0177271 | A1 | 7/2012 | Johnston |
| 2013/0195341 | A1 | 8/2013 | Liu |
| 2014/0270448 | A1 | 9/2014 | Mok |
| 2014/0343401 | A1 | 11/2014 | Huber |

FOREIGN PATENT DOCUMENTS

| | | |
|---|---|---|
| WO | 2005/067605 | 7/2005 |
| WO | 2007/136967 | 11/2007 |
| WO | 2012/142031 | 10/2012 |
| WO | 2014165979 | 10/2014 |

OTHER PUBLICATIONS

Hwang, et al., "Robust real-time respiratory motion tracking using ultrasound image sequences"; Ultrasonics Symposium, 2012 IEEE International.

Xu, et al., "A novel respiratory detection method based on automated analysis of ultrasound diaphragm video"; Medical Physics, vol. 33, No. 4, Mar. 16, 2006.

Timinger, et al., "Motion compensated coronary interventional navigation by means of diaphragm tracking and elastic motion models"; Phys Med Biol. Feb. 7, 2005;50(3):491-503.

Cervino, et al., "The diaphragm as an anatomic surrogate for lung tumor motion"; Phys. Med. Biol. 54 (2009) 3529-3541.

* cited by examiner

RESPIRATORY MOTION COMPENSATION FOR FOUR-DIMENSIONAL COMPUTED TOMOGRAPHY IMAGING USING ULTRASOUND

CROSS REFERENCE TO RELATED APPLICATIONS

This application is the U.S. National Phase application under 35 U.S.C. § 371 of International Application No. PCT/IB2016/055296, filed Sep. 5, 2016, published as WO 2017/046674 filed Mar. 23, 2017, which claims the benefit of U.S. Provisional Patent Application Number 62/219,184 filed Sep. 16, 2015. These applications are hereby incorporated by reference herein.

FIELD OF THE INVENTION

The following generally relates to computed tomography and more particularly to respiratory motion compensation for four-dimensional computed tomography (4D CT) imaging using ultrasound. The following is also amenable to other imaging modalities.

BACKGROUND OF THE INVENTION

Figure 1:
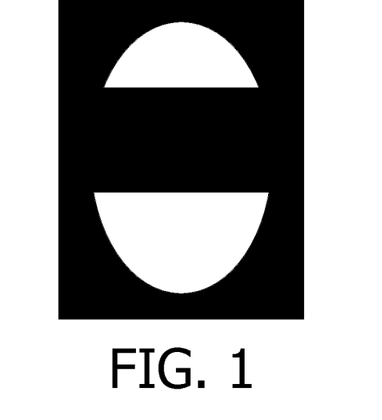
FIG. 1 show geometric distortion of an object of interest in four static CT images.

Motion due to the respiratory cycle (i.e., inhalation and exhalation of the lungs) can cause severe distortion in the geometry of target tissue of interest during a free-breathing static computed tomography (CT) scan. Free-breathing generally means the patient breathes during scanning. That is, the patient is not required to hold their breath. Static refers to the patient support being held at a same static position for the scan. The motion induced distortions can randomly shorten or lengthen the target tissue of interest. The distortions can also dislocate the center of the target tissue of interest. FIG. 1 show geometric distortion of an object of interest in a static CT image.

Because of these distortions, a free-breathing static CT scan is not well suited for dose planning for radiation therapy, especially for lung cancer tumors. 4D CT is an approach which mitigates this shortcoming. In 4D CT, the patient is over sampled along his/her long axis at every subject support position of interest. Each CT slice is then correlated with a breathing phase of the respiratory cycle. The CT slices with similar breathing phase but acquired at different couch positions are binned together, sorted based on the couch position, and concatenated into a 3D image. As such, 4D CT volume is a series of static CT images acquired at different breathing phases.

In order to measure the breathing phase, a surrogate respiratory signal is used. One surrogate is determined via spirometry. In spirometry, the flow of air in and out of the lung is measured by breathing through a device that has a turbine-shaped fan enclosed in a tube. The rate of rotation of the fan determines the air flow rate and is measured as a respiratory signal. Another surrogate is to track reflective markers placed on the patient's chest or abdomen. The reflective markers move as the patient breath and their motion can be used as a respiratory signal. Another surrogate is an air-bellow belt that captures the change in abdomen size during breathing.

Figure 2:
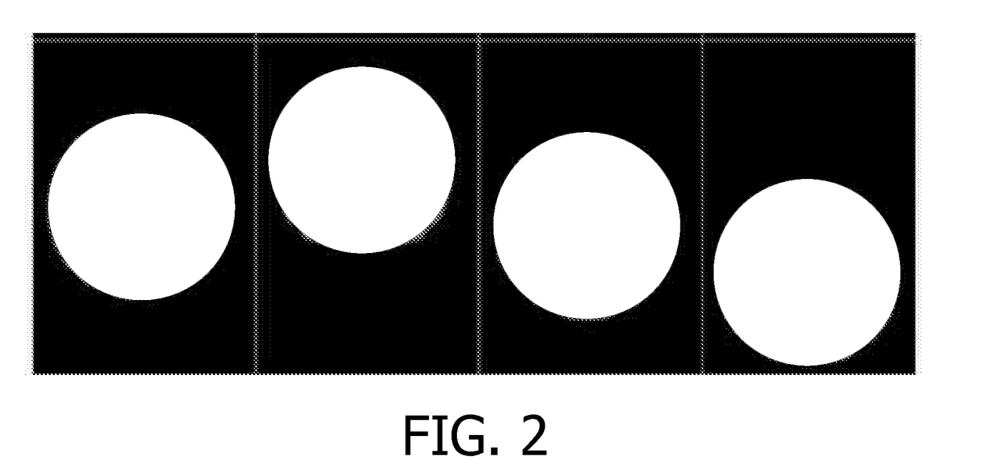
FIG. 2 shows an example of motion artifact over four different phases of a 4D CT with the target at different locations.
Figure 3:
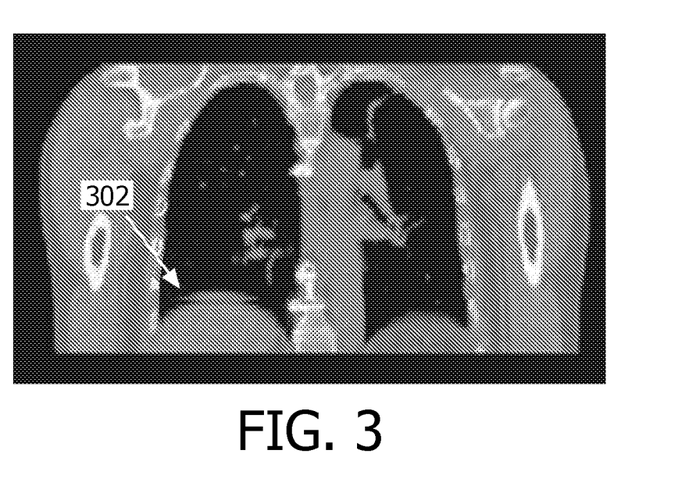
FIG. 3 shows a 4D CT image of the lungs, chest, and shoulder of a patient with example motion artifact.

Unfortunately, the above-noted approaches do not correlate well with the actual breathing phases of the respiratory cycle of a patient. As a consequence, 4D CT volumes often contain motion artifacts. FIG. 2 shows an example of motion artifact over four different phases of a 4D CT where the target is depicted at different locations in each image. FIG. 3 shows a 4D CT image of the lungs, chest, and shoulder of a patient with example motion artifact 302. In view of at least the above, there is an unresolved need for another approach for determining a motion signal that correlates well with the actual breathing phases of the respiratory cycle of a patient.

SUMMARY OF THE INVENTION

Aspects of the present application address the above-referenced matters and others.

According to one aspect, a method for determining a surrogate respiratory signal for four-dimensional computed tomography using ultrasound data includes, acquiring computed tomography data with a computed tomography imaging system, acquiring ultrasound data with an ultrasound probe of an ultrasound imaging system concurrently with acquiring the computed tomography data during one or more respiratory cycles, wherein the ultrasound probe is aligned to acquire an image of a diaphragm of a subject, synchronizing the acquired computed tomography data and the acquired ultrasound data, and determining a surrogate respiratory signal from the acquired ultrasound data.

In another aspect, a system includes computed tomography imaging system, an ultrasound imaging system, and a data synchronization and four dimensional computed tomography volume processor. The computed tomography imaging system and the ultrasound imaging system are configured to concurrently acquire computed tomography imaging data and ultrasound imaging data. The data synchronization and four dimensional computed tomography volume processor is configured to transform the ultrasound imaging data and determine a surrogate respiratory cycle signal representing an actual respiratory cycle of a scanned patient. The data synchronization and four dimensional computed tomography volume processor is configured to transform the computed tomography imaging data using the surrogate respiratory cycle signal to construct four dimensional computed tomography data.

In another aspect, a computer readable storage medium is encoded with computer readable instructions, which, when executed by a processor of a computing system, causes the processor to: concurrently acquire computed tomography data and ultrasound data, determine a surrogate respiratory signal from the ultrasound data, synchronize the acquired computed tomography data and the acquired ultrasound data, bin image slices of the computed tomography data that have a similar amplitude or phase based on the surrogate respiratory signal, sort the binned image slices based a subject support position, and combine the sorted image slices by concatenating the sorted images into a three dimensional volume corresponding to a respiratory phase.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 4:
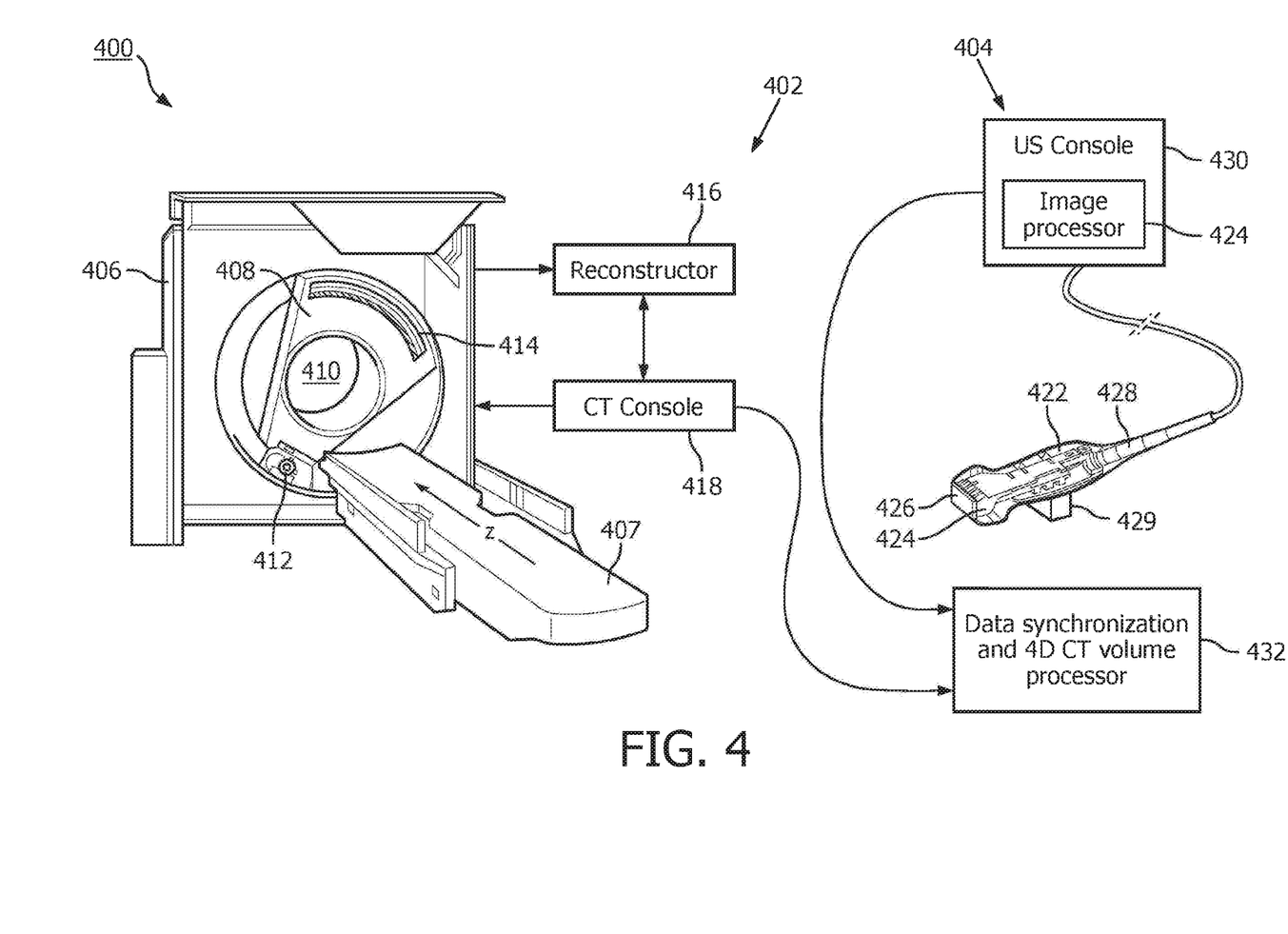
FIG. 4 schematically illustrates a system including a CT imaging system, an US imaging system, and a data synchronization and 4D CT volume processor.

FIG. 4 schematically illustrates a system 400 including a CT imaging system 402 and an ultrasound (US) imaging system 404. The CT imaging system 402 includes a generally stationary gantry 406 and a rotating gantry 408, which is rotatably supported by the stationary gantry 406 and rotates around an examination region 410 about a z-axis. A subject support 407, such as a couch, supports an object or subject in the examination region 410.

A radiation source 412, such as an x-ray tube, is rotatably supported by the rotating gantry 408, rotates with the rotating gantry 408, and emits radiation that traverses the examination region 410. A radiation sensitive detector array 414 subtends an angular arc opposite the radiation source 412 across the examination region 410. The radiation sensitive detector array 414 detects radiation traversing the examination region 410 and generates projection data, or a signal indicative thereof for each detected radiation.

A reconstructor 416 reconstructs the signal and generates volumetric image data indicative of a scanned portion of a subject or object located in the examination region 410. A CT console 418 includes a human readable output device such as a monitor and an input device such as a keyboard, mouse, etc. Software resident on the CT console 418 allows the operator to interact with and/or operate the CT imaging system 402 via a graphical user interface (GUI) or otherwise.

The US imaging system 404 includes a probe 422 housing a transducer array 424. The transducer array 424 includes an array of transducer elements, each configured to transmit US signals through an acoustic window 426 and receive echo signals, which are created in response to the US signals interacting with structure in a field of view. The transducer array 424 is configured to acquire data which can be processed to generate a 1D, 2D and/or 3D data. This includes single element imaging in M-mode, 2D imaging in B-mode, or 3D matrix imaging in B-mode.

In the illustrated example, the probe 422 is supported by a device 429, which supports and maintains the probe 422 at a static known position during breathing and scanning. Alternatively, the probe 422 is attached to an encoded arm to measure its movement during breathing using the arm encoders. Alternatively, the probe 422 is supported and guided by a robotic arm. Alternatively, a tracking system employing optical, electromagnetic (EM), etc. tracking, optical shape sensing, etc. is utilized to track the probe 422. An example of EM tracking is described in PCT/IB2013/054405, filed Dec. 28, 2013, the entirety of which is incorporated herein by reference.

In the illustrated example, the probe 422 interfaces through a cable 428 with a US console 430. Alternatively, the probe 422 may include a wireless interface. The US console 430, similar to the CT console 418, includes a human readable output device such as a monitor and an input device such as a keyboard, mouse, etc. Furthermore, like the CT console 418, software resident on the US console 430 allows the operator to interact with and/or operate the US imaging system 404 via a graphical user interface (GUI) or otherwise.

A data synchronization and 4D CT volume processor 432 processes CT data acquired by the CT imaging system 402 and US data acquired by the US imaging system 404. Where a tracking system is used to track the location of the transducer array 424, tracking information is also provided to the data synchronization and 4D CT volume processor 432. From this data, the data synchronization and 4D CT volume processor 432 associates each CT slice with US data (1D, 2D or 3D), a CT couch position, and a transducer array position/orientation (if available). This can be based on time stamps in the data, synchronizes clocks, a single clock, and/or otherwise.

As described in greater detail below, the data synchronization and 4D CT volume processor 432 processes the US data and generates a surrogate respiratory signal therefrom, which represents the phases of the respiratory cycles. The data synchronization and 4D CT volume processor 432 uses this surrogate respiratory signal to sort and combine the CT slices to generate the 4D CT volume. Since the surrogate respiratory signal reflects the actual movement of the diaphragm, the surrogate respiratory signal correlates well with the actual respiratory cycle, mitigating motion signal associated with using spirometry, markers, a belt, and other approaches which yield signals that do not correlate well with the actual respiratory cycle, introducing motion artifact.

Figure 5:
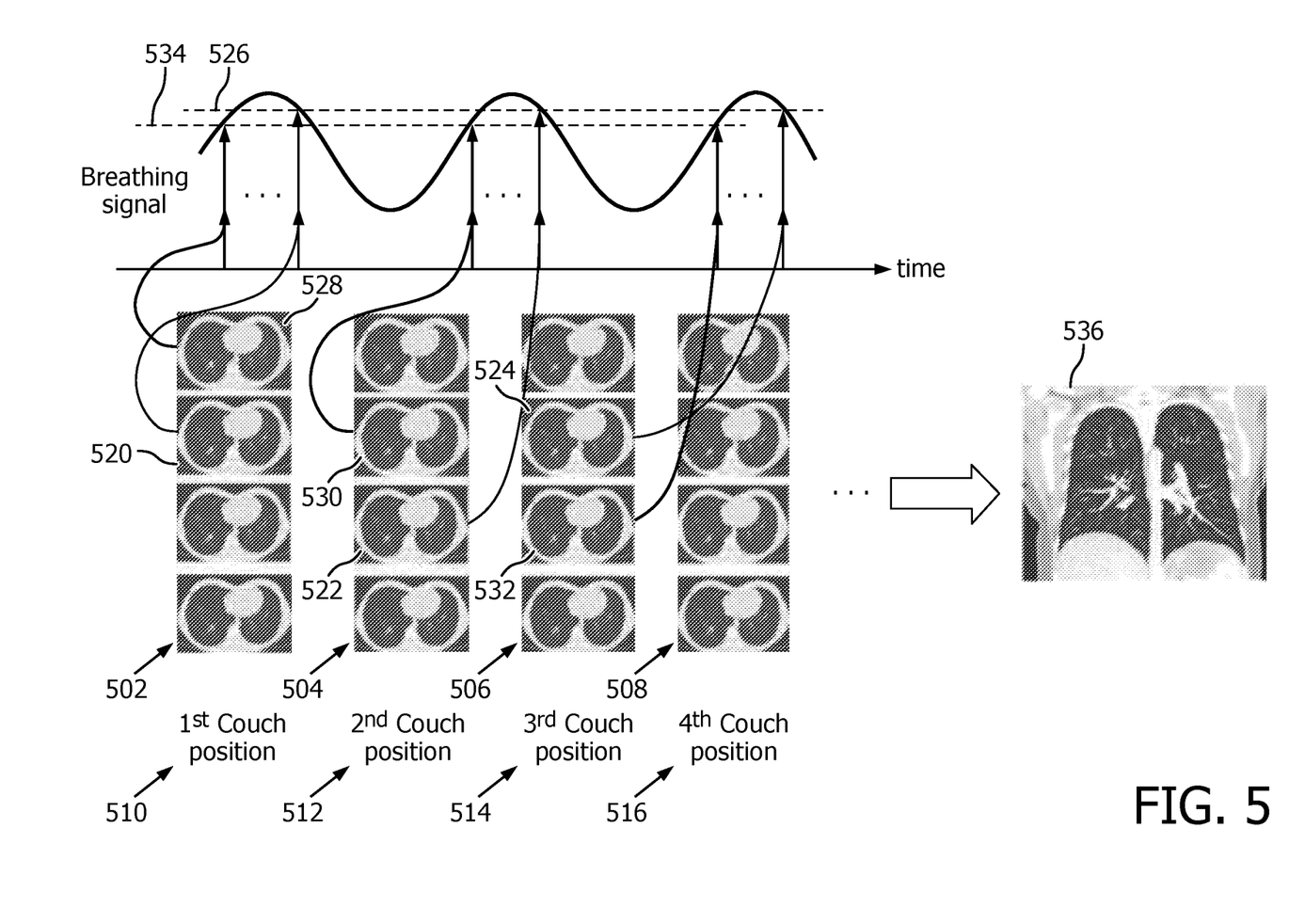
FIG. 5 illustrates an example of sorting and combining data to generate 4D CT data.

An example of the sorting and combining to generate 4D CT data is shown in FIG. 5. In FIG. 5, multiple sets CT slices 502, 504, 506, 508, . . . are acquired at couch positions 510, 512, 514, 516, . . . . Each image corresponds to a respiratory phase/amplitude. The slices that have similar (same or within ±10%) breathing signal phase/amplitude are binned (e.g., slices 520, 522 and 524 having amplitude 526 are binned, slices 528, 530 and 532 having amplitude 534 are binned, etc.) together and sorted based on their couch position. The data synchronization and 4D CT volume processor 432 concatenates the images into a 3D volume 536 corresponding to a signal phase and displays the result.

In the illustrated embodiment, the data synchronization and 4D CT volume processor 432 is part of a computing system (with a processor, memory, etc.) separate from the CT imaging system 402 and the US imaging system 404. In another embodiment, the data synchronization and 4D CT volume processor 432 is part of the CT imaging system console 418 and/or the US imaging system console 430. In yet another embodiment, the data synchronization and 4D CT volume processor 432 is distributed across the CT imaging system 402 and/or the US imaging system 404 and one or more other computing systems.

The CT volumetric data, the US data (1D, 2D and/or 3D), the tracking data (if acquired), the surrogate respiratory signal, the 3D volume 536, the 4D CT data, and/or other data can be stored in a data repository as electronically formatted data. Examples of a suitable data repository include a picture archiving and communication system (PACS), radiology information system (RIS), a hospital information system (HIS), an electronic medical record (EMR), a database, a server, etc. This data can also be stored with the CT imaging system 402 and/or the US imaging system 404.

Figure 6:
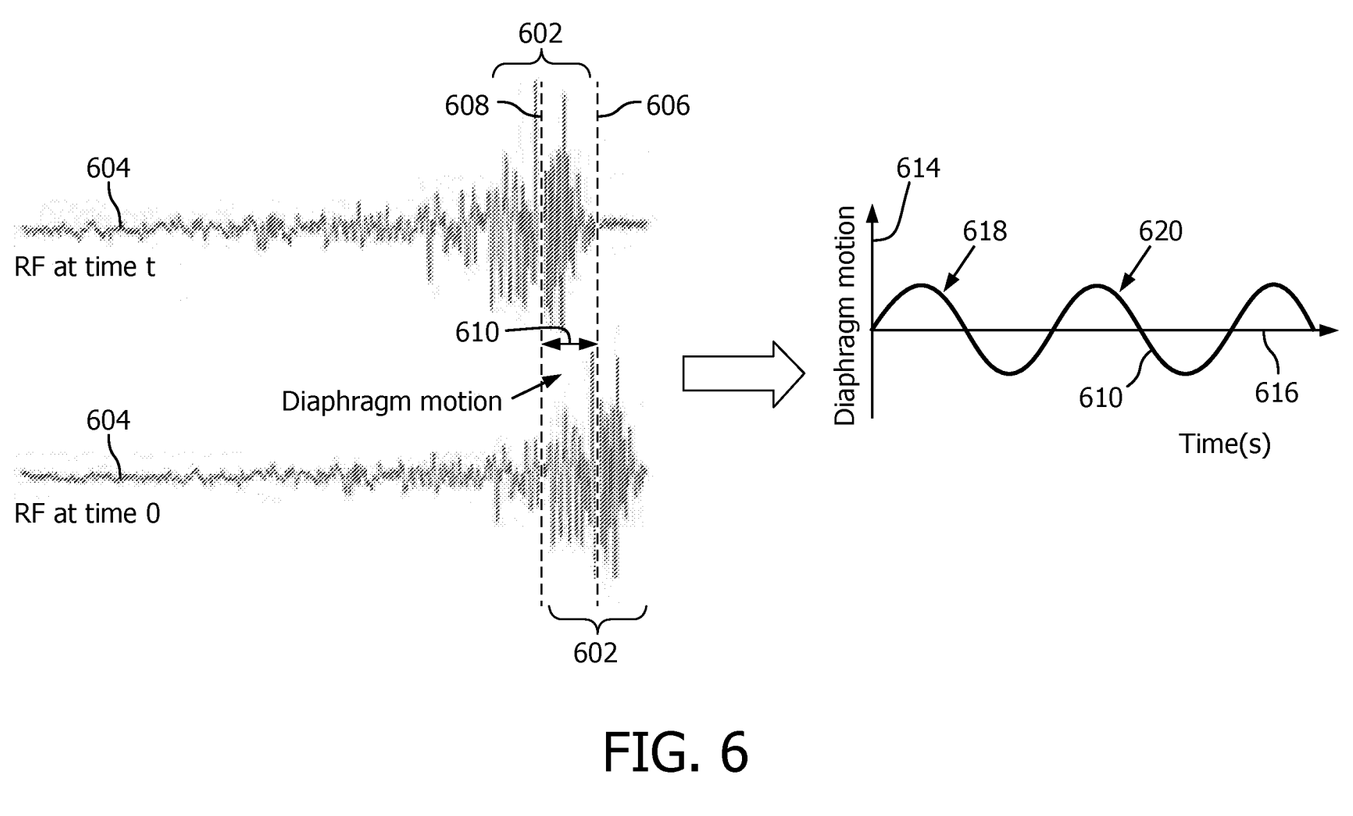
FIG. 6 illustrates a high intensity sub-portion of 1D RF data as a function of respiratory phase.

As briefly described above, the data synchronization and 4D CT volume processor 432 processes the US data to generate a surrogate repository signal therefrom. The following describes non-limiting examples using 1D, 2D and 3D US data to generate a surrogate repository signal.

Where a single-transducer element is used in M-mode to acquire data, the acquired US data will include high intensity sub-portion in the RF data corresponding to the diaphragm interface, which is hyper-echoic. As example of this is shown in FIG. 6, where a high intensity sub-portion 602 of RF data 604 is centered about a location 606 at t=0.

The high intensity sub-portion 602 will move in the RF data 604 during the respiratory cycle. An example of this is also shown in FIG. 6, where the sub-portion 602 is shifted and is now centered about a location 608 at t=x. The difference between the locations 606 and 608 represents a shift 610 and corresponds to diaphragm motion, or the respiratory cycle. FIG. 6 also shows a plot of motion 614 (i.e., the shift 610) relative to the location 606 over time 616 for multiple respiratory cycles 618, 620 . . . relative to a base line respiratory phase.

In this example, the movement of the high intensity sub-portion 602 in the RF data 604 (e.g., the shift 610) is used as indicator of diaphragm movement and used as the surrogate for the respiratory cycle. Known and/or other motion detection algorithms can be used for motion detection of 602 in the RF data 604 such as cross-correlation or 1D Demons. In this example, the single element transducer can be fixed in space relative to the patient's body (as shown in FIG. 4), as discussed herein.

Where 2D US images is acquired in B-mode during CT scanning, each CT slice is associated with one B-mode image. The surrogate signal is then generated based on one or more approaches.

Figure 7:
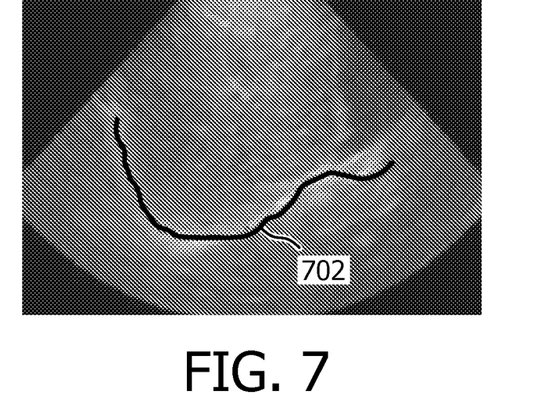
FIG. 7 illustrates a segmented diaphragm surface in 2D ultrasound image data.

With one approach, the diaphragm surface is segmented in the B-mode images. An example of this is shown in FIG. 7. In FIG. 7, a surface 702 represents the segmented diaphragm. Diaphragm motion is then measured and compared via a baseline, either through an absolute distance measurement between diaphragm position in time t and the baseline diaphragm position at time 0, or by a summation of incremental diaphragm motions between time t and t−1.

In another approach, a cross correlation of B-mode image at time t and the baseline B-mode image (at time 0) is computed, and the cross correlation value is utilized as the surrogate signal. With this approach, as the diaphragm moves it results in a decorrelation between the image at time t and the baseline image. In both cases the probe 422 is either preferably fixed relative to the patient's body or tracked, as described herein.

Where 3D US volumetric image data is acquired in B-mode during CT scanning each CT slice is associated with a B-mode volume. The surrogate signal is generated based on one or more approaches.

With one approach, the diaphragm surface is segmented in the B-mode volume. The diaphragm motion is then measured and compared to a baseline volume, either through absolute distance measurement between diaphragm position in time t and the baseline diaphragm position at time 0, or by summation of incremental diaphragm motions between time t and t−1.

In another approach, a cross correlation of B-mode volume at time t and the baseline B-mode volume (at time 0) is computed, and the cross correlation value is utilized as the surrogate signal. With this approach, as the diaphragm moves it results in a decorrelation between the image at time t and the baseline image. In both cases the probe 422 is either fixed or tracked, as described herein.

Figure 8:
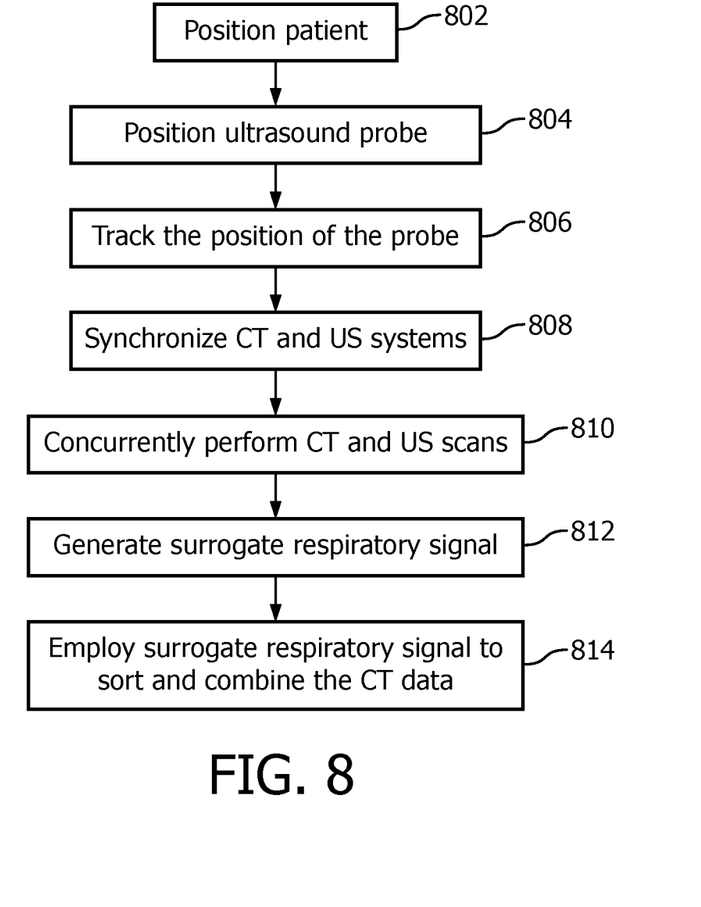
FIG. 8 illustrates an example method respiratory motion compensation for 4D CT using ultrasound.

FIG. 8 illustrates an example method of generating and using a respiratory signal using a single transducer array 424 element in M-mode.

It is to be appreciated that the ordering of the above acts is not limiting. As such, other orderings are contemplated herein. In addition, one or more acts may be omitted and/or one or more additional acts may be included.

At 802, a patient is positioned on the subject support 420 in the examination region 410 for a scan.

At 804, the ultrasound probe 422 of the ultrasound imaging system 404 is suitably positioned on the patient to acquire an image of the diaphragm (e.g., intercostal or subcostal are two possibilities).

At 806, the location of the ultrasound probe 422 with respect to the subject is tracked or fixed, as discussed herein and/or otherwise.

At 808, the CT imaging system 102 and the US imaging system 104 are interfaced with the data synchronization and 4D CT volume processor 432.

At 810, a CT scan and a US scan are concurrently performed while the patient normally breathes.

At 812, a surrogate respiratory signal is generated from the acquired US data. As described herein, the surrogate respiratory signal can be generated from 1D, 2D and/or 3D US data.

At 814, the data synchronization and 4D CT volume processor 432 employs the surrogate respiratory signal to sort and combine the CT slices to generate 4D CT volumetric data.

The above may be implemented by way of computer readable instructions, encoded or embedded on non-transitory computer readable storage medium (physical memory, and excluding signals, carrier waves and other transitory medium), which, when executed by a computer processor(s) (e.g., a microprocessor, a controller, etc.), cause the computer processor(s) to carry out the described acts. Additionally or alternatively, at least one of the computer readable instructions is carried by a signal, carrier wave or other transitory medium.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method for compensating a respiratory motion in four-dimensional computed tomography using ultrasound data, comprising:
  acquiring computed tomography data with a computed tomography imaging system;
  acquiring the ultrasound data with an ultrasound probe of an ultrasound imaging system concurrently with acquiring the computed tomography data during one or more respiratory cycles, wherein the ultrasound probe is aligned to acquire an image of a diaphragm of a subject, and wherein the acquired ultrasound data includes one dimensional radio frequency data;
  synchronizing the acquired computed tomography data and the acquired ultrasound data; and
  determining a surrogate respiratory signal from the acquired ultrasound data by:

identifying a high intensity sub-portion of the one dimensional radio frequency data as a baseline portion;

tracking a movement of the high intensity sub-portion relative to the baseline portion over the respiratory cycle; and generating the surrogate respiratory signal based on the tracked movement.

2. The method of claim 1, further comprising:

sorting the computed tomography data using the surrogate respiratory signal; and combining the sorted computed tomography data to generate the four-dimensional computed tomography.

3. The method of claim 2, further comprising binning image slices of the computed tomography data that have a similar amplitude based on the surrogate respiratory signal; sorting the binned images slices based on subject support position; and concatenating the sorted images into the four-dimensional computed tomography.

4. The method of claim 1, further comprising:

maintaining the ultrasound probe at a fixed position while acquiring the ultrasound data; or tracking a movement of the ultrasound probe while acquiring the ultrasound data.

5. A method for compensating a respiratory motion in four-dimensional computed tomography using ultrasound data, comprising:

acquiring computed tomography data with a computed tomography imaging system;

acquiring the ultrasound data with an ultrasound probe of an ultrasound imaging system concurrently with acquiring the computed tomography data during one or more respiratory cycles, wherein the ultrasound probe is aligned to acquire an image of a diaphragm of a subject, and wherein the acquired ultrasound data includes two dimensional ultrasound images;

synchronizing the acquired computed tomography data and the acquired ultrasound data; and determining a surrogate respiratory signal from the acquired ultrasound data by:

segmenting a diaphragm surface in the two dimensional ultrasound images;

identifying the segmented diaphragm surface as a baseline segmented diaphragm portion;

tracking a movement of the segmented diaphragm surface relative to the baseline segmented diaphragm portion over the respiratory cycle; and comparing the tracked segmented diaphragm surface through at least one of:

an absolute distance measurement between a diaphragm position at a first time and a baseline diaphragm position at a second time; and a summation of incremental diaphragm motions between a first time and a previous time.

6. The method of claim 5, further comprising:

maintaining the ultrasound probe of the ultrasound imaging system at a fixed position while acquiring the ultrasound data; or tracking a movement of the ultrasound probe while acquiring the ultrasound data.

7. A method for compensating a respiratory motion in four-dimensional computed tomography using ultrasound data, comprising:

acquiring computed tomography data with a computed tomography imaging system;

acquiring the ultrasound data with an ultrasound probe of an ultrasound imaging system concurrently with acquiring the computed tomography data during one or more respiratory cycles, wherein the ultrasound probe is aligned to acquire an image of a diaphragm of a subject, and wherein the acquired ultrasound data includes two dimensional ultrasound images synchronizing the acquired computed tomography data and the acquired ultrasound data; and determining a surrogate respiratory signal from the acquired ultrasound data by:

computing a cross correlation value of a two dimensional ultrasound image at a first time with a baseline two dimensional ultrasound image at a second time; and using the cross correlation value as the surrogate respiratory signal.

8. The method of claim 7, further comprising:

maintaining the ultrasound probe of the ultrasound imaging system at a fixed position while acquiring the ultrasound data; or tracking a movement of the ultrasound probe while acquiring the ultrasound data.

9. A method for compensating a respiratory motion in four-dimensional computed tomography using ultrasound data, comprising:

acquiring computed tomography data with a computed tomography imaging system;

acquiring the ultrasound data with an ultrasound probe of an ultrasound imaging system concurrently with acquiring the computed tomography data during one or more respiratory cycles, wherein the ultrasound probe is aligned to acquire an image of a diaphragm of a subject, and wherein the acquired ultrasound data includes three dimensional ultrasound volume;

synchronizing the acquired computed tomography data and the acquired ultrasound data; and determining a surrogate respiratory signal from the acquired ultrasound data by:

segmenting a diaphragm surface in the three dimensional ultrasound volume;

identifying the segmented diaphragm surface as a baseline segmented diaphragm portion;

tracking a movement of the segmented diaphragm surface relative to the baseline segmented diaphragm portion over the respiratory cycle;

comparing the tracked segmented diaphragm surface through at least one of:

an absolute distance measurement between a diaphragm position at a first time and a baseline diaphragm position at a second time; and a summation of incremental diaphragm motions between a first time and a previous time.

10. The method of claim 9, further comprising:

maintaining the ultrasound probe of the ultrasound imaging system at a fixed position while acquiring the ultrasound data; or tracking a movement of the ultrasound probe while acquiring the ultrasound data.

11. A method for compensating a respiratory motion in four-dimensional computed tomography using ultrasound data, comprising:

acquiring computed tomography data with a computed tomography imaging system;

acquiring the ultrasound data with an ultrasound probe of an ultrasound imaging system concurrently with acquiring the computed tomography data during one or more respiratory cycles, wherein the ultrasound probe is aligned to acquire an image of a diaphragm of a subject, and wherein the acquired ultrasound data includes three dimensional ultrasound volume;
synchronizing the acquired computed tomography data and the acquired ultrasound data; and
determining a surrogate respiratory signal from the acquired ultrasound data by:
computing a cross correlation value of the three dimensional ultrasound volume at a first time with a baseline three dimensional ultrasound volume at a second time; and
using the cross correlation value as the surrogate respiratory signal.

12. The method of claim 11, further comprising:
maintaining the ultrasound probe of the ultrasound imaging system at a fixed position while acquiring the ultrasound data; or
tracking a movement of the ultrasound probe while acquiring the ultrasound data.

13. A system for compensating a respiratory motion in four-dimensional computed tomography using ultrasound data, comprising:
a computed tomography imaging system configured to acquire computed tomography data;
an ultrasound imaging system comprising an ultrasound probe configured to acquire the ultrasound data concurrently with acquiring the computed tomography data during one or more respiratory cycles, wherein the ultrasound probe is aligned to acquire an image of a diaphragm of a subject, and wherein the acquired ultrasound data includes one dimensional radio frequency data; and
at least one processor configured to:
synchronize the acquired computed tomography data and the acquired ultrasound data; and
determine the surrogate respiratory signal from the acquired ultrasound data by:
identifying a high intensity sub-portion of the one dimensional radio frequency data as a baseline portion;
tracking a movement of the high intensity sub-portion relative to the baseline portion over the respiratory cycle; and
generating the surrogate respiratory signal based on the tracked movement.

14. The system of claim 13, wherein the ultrasound probe is maintained at a fixed position while acquiring the ultrasound data; or a movement of the ultrasound probe is tracked while acquiring the ultrasound data.

15. The system of claim 13, wherein the at least one processor is further configured to:
sort the computed tomography data using the surrogate respiratory signal; and
combine the sorted computed tomography data to generate the four-dimensional computed tomography.

16. The system of claim 15, wherein the at least one processor is further configured to:
bin image slices of the computed tomography data that have a similar amplitude based on the surrogate respiratory signal;
sort the binned images slices based on subject support position; and
concatenate the sorted images into the four-dimensional computed tomography.

* * * * *